United States Patent [19]

Kakimoto et al.

[11] Patent Number: 4,956,272

[45] Date of Patent: Sep. 11, 1990

[54] ORGANOGERMANIUM CONTAINING SOLUTION FOR WASHING AND STORING SEPARATED ORGANS

[75] Inventors: Norihiro Kakimoto, Machida; Kazuo Kumano, Yamato; Kunie Nakamura, Sagamihara, all of Japan

[73] Assignee: Asai Germanium Research Institute Co., Ltd., Tokyo, Japan

[21] Appl. No.: 261,628

[22] Filed: Oct. 24, 1988

[30] Foreign Application Priority Data

Oct. 29, 1987 [JP] Japan .................................. 62-273745

[51] Int. Cl.$^5$ .............................................. A01N 1/02
[52] U.S. Cl. .......................................... 435/1; 556/87
[58] Field of Search ............................... 556/87; 435/1

[56] References Cited

U.S. PATENT DOCUMENTS 3,689,516  9/1972  Asai et al. .............................. 556/87
4,066,678  1/1978  Sato et al. ............................. 556/87

*Primary Examiner*—Sam Rosen

*Attorney, Agent, or Firm*—Burns, Doane, Swecker & Mathis

[57] ABSTRACT

The present invention provides (1) a solution for washing and storing separated organs, characterized by containing, as an effective component, an organogermanium compound represented by the formula (I)

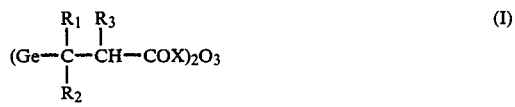

wherein $R_1$ to $R_3$ are each a hydrogen atom, a lower alkyl group such as methyl, ethyl or the like which may be the same or different, or a substituted or unsubstituted phenyl group, and X is a hydroxyl group, an O-lower alkyl group, an amino group or $O^-Y^+$ (Y is a metal such as sodium, potassium or the like, or a basic group-containing compound such as lysozyme, basic amino acid or the like), and (2) a method for washing and storing separated organs with a solution containing, as an effective component, an organogermanium compound represented by the formula (I).

16 Claims, No Drawings

1

ORGANOGERMANIUM CONTAINING SOLUTION FOR WASHING AND STORING SEPARATED ORGANS

BACKGROUND OF THE INVENTION

1. Field of the Invention

The present invention relates to a solution for washing and storing organs, particularly kidneys separated from living bodies. More particularly, the present invention relates to a solution for washing and storing separated organs, which contains a particular organogermanium compound as an effective component.

2. Description of the Prior Art

Reduced functions of an organ in a living body result in various diseases and at times even death. In this case, it is necessary to take appropriate measures.

In such a case, it is a general practice to administer an appropriate drug to a living body having an organ with reduced functions in order to restore the original functions by an internal treatment, or to use an appropriate supplementary means to compensate for the reduced functions, whereby the overall functions of the living body are maintained. When no appropriate drug is available or the use of the supplementary means produces a disturbance, however, it is not rare to conduct an organ transplant wherein the organ in question is enucleated and replaced by a corresponding organ taken out from another living body.

Liver or heart transplants are conducted based on the death of a donor, and the determination of the timing of his or her death has been a big social dispute in some countries. In contrast, kidney transplant does not affect the life of a donor in principle; accordingly, there are about 650 operational cases of kidney transplants per year in Japan alone, for example.

Of the above operational cases for kidney transplant in Japan, 150 cases are cadaveric kidney transplants and the remaining are living kidney transplants. In any of these transplants, the interior and exterior of an enucleated kidney are washed by a washing and storing solution, i.e. a crystalloid solution such as a Collins solution, an Euro Collins solution or the like; then the kidney is stored in the same washing and storing solution at low temperatures until it is transplanted. Naturally, the washing and storing solution has an negligible adverse effect on the outcome of transplant operations; therefore, the washing and storing solution must have such a property that gives little adverse effect on the functions, tissue, etc. of a kidney to be stored in the solution.

The above-mentioned Collins solution is an electrolyte solution developed by G. M. Collins and others, having the same composition as intracellular fluid [Lancet, 2, 1219 (1969) and Lancet, 1, 1024 (1973)] and has been preferably used in kidney transplants. It was pointed out, however, that the magnesium ion contained in the Collins solution causes precipitation.

Then an Euro Collins solution containing no magnesium ion was developed. Its usefulness has been supported not only by basic study but also by clinical application.

In view of the importance of kidney-washing and storing for kidney transplant operations, there is a need in the art to develop a kidney-washing and storing solution of higher effect.

SUMMARY OF THE INVENTION

Considering the above situation of the prior art, the present invention has been made in order to provide a solution for washing and storing separated organs, which gives, during washing and storing, a less adverse effect on separated organs than the conventional Collins or Euro Collins solution.

The concept adopted by the present invention in order to achieve the above objects lies in a solution for washing and storing separated organs, characterized by containing, as effective component, an organogermanium compound represented by the formula (I)

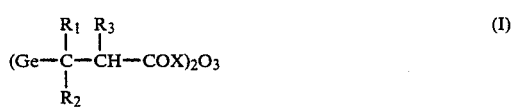

wherein $R_1$ to $R_3$ are each a hydrogen atom, a lower alkyl group such as methyl, ethyl or the like which may be the same or different, or a substituted or unsubstituted phenyl group, and X is a hydroxyl group, an O-lower alkyl group, an amino group or $O^-Y^+$ (Y is a metal such as sodium, potassium or the like, or a basic group-containing compound such as lysozyme, basic amino acid or the like).

DETAILED DESCRIPTION OF THE PREFERRED EMBODIMENTS

The solution for washing and storing organs according to the present invention contains, as an effective component, a particular organogermanium compound represented by the formula (I). Hence, this compound is explained first. The compound has, as its basic skeleton, a germylpropionic acid formed by the bonding of a germanium atom and a propionic acid derivative having three substituents $R_1$ to $R_3$ and an oxygen functional group OX, in which basic skeleton of the germanium atom and the oxygen atom is 2:3.

The substituents $R_1$ to $R_3$ are each a hydrogen atom, a lower alkyl group such as methyl, ethyl, propyl, butyl or the like, or a substituted or unsubstituted phenyl group; the substituent X is a hydroxyl group, an O-lower alkyl group, an amino group or a salt of carboxylic acid represented by $O^-Y^+$.

Y is a metal such as sodium, potassium or the like (the metal is not restricted to a monovalent metal), or a basic group containing compound such as lysozyme, basic amino acid such as lysine or the like.

The substituents $R_1$ and $R_2$ bond to the α-position of the germanium atom and the substituent $R_3$ bonds to the β-position of the germanium atom. Accordingly, specific examples of the organogermanium compound used in the solution for washing and storing organs according to the present invention are as follows.

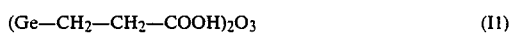

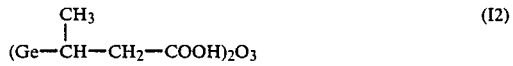

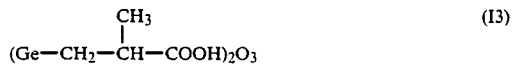

-continued

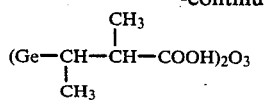  (I4)

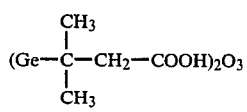  (I5)

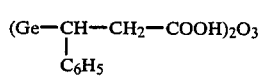  (I6)

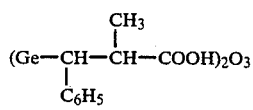  (I7)

(Ge—CH$_2$—CH$_2$—COOCH$_3$)$_2$O$_3$  (I8)

(Ge—CH$_2$—CH$_2$—CONH$_2$)$_2$O$_3$  (I9)

(Ge—CH$_2$—CH$_2$—COO$^-$Na$^+$)$_2$O$_3$  (I10)

The organogermanium compounds having the above structures can be produced according to various methods.

Those compounds of the formula (I) wherein X=OH can be produced, for example, by hydrolyzing a trihalogermylpropionic acid already having three substituents R$_1$ to R$_3$, such as trichlorogermylpropionic acid (1), as shown in the following reaction formula.

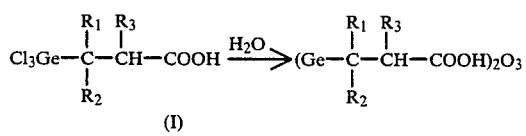

Those compounds of the formula (I) wherein X=a lower alkyl group can be produced, for example, by reacting the above compound (I) with thionyl chloride or the like to convert the former to a corresponding acid halide, reacting the acid halide with an alcohol corresponding to the lower alkyl group, and then hydrolyzing the reaction product. Those compounds of the formula (I) wherein X=NH$_2$ can be produced, for example, by reacting the above acid halide with NH$_3$ and then hydrolyzing the reaction product. Those compounds of the formula (I) wherein X=O$^-$Y$^+$ and Y=a metal can be produced by reacting above compound (1) with a corresponding metal hydroxide. Those compounds of the formula (I) wherein X=O$^-$Y$^+$ and Y=a basic group-containing compound can be produced according to an ordinary acid-base reaction.

The analytical result obtained for the produced organogermanium compounds according to instrumental analysis methods such as NMR spectrometry, infrared spectroscopy and the like well support that the compounds represented by the general formula (I) and the solution for washing and storing separated organs of the present invention contain, as an effective component, a particular organogermanium compound obtained by the above synthesis.

Apparently, a solution merely containing the organogermanium compound of the formula (I) is not a hypertonic electrolyte solution having the same composition as intracellular fluid, used in organ washing and storing. Therefore, the washing and storing solution of the present invention further contains potassium hydrogenphosphate, potassium dihydrogenphosphate, etc. and can be produced, when done simply, by merely adding the above-mentioned organogermanium compound to a conventional organ washing and storing solution (e.g. Collins solution, Euro Collins solution) in an appropriate proportion, for example, about 0.5-1% by weight/volume.

The organ washing and storing of the present invention gives a less adverse effect on a separated organ to be stored therein than the conventional Collins or Euro Collins solution and therefore is superior to the latter. In experiments of kidney enucleation, storage and transplant for dogs, the present solution showed a far higher survival rate after transplant than the ordinary kidney-storing solution.

The effects of the present solution are shown below by way of Example.

(1) Test animal

Mongrel dogs weighing about 10 Kg were used.

(2) Test method

One kidney of each mongrel dog was enucleated. Two solutions for washing and storing kidneys, having the following compositions were prepared.

| Solution of composition 1 (conventional solution) | |
|---|---|
| Euro Collins solution (product of Midori Juji Co., Ltd.) | 500 ml |
| Heparin | 5 ml (5,000U) |
| Procaine (2%) | 2 ml |
| Lasix (trade name) | 1 ml |
| Mannitol (20%) | 50 ml |
| Solution of composition 2 (present solution) | |
| Same components as in composition 1 solution | Same quantities as above |
| Organogermanium compound of formula (I-1) | 5 g |

The above Euro Collins solution is a solution for washing and storing separated kidneys and has the following electrolyte composition.

| | |
|---|---|
| Na$^+$ | 10 mEq/l |
| K$^+$ | 115 mEq/l |
| Cl$^-$ | 15 mEq/l |
| HCO$_3^-$ | 10 mEq/l |
| HPO$_4^{--}$ | 80 mEq/l |
| H$_2$PO$_4^-$ | 15 mEq/l |

The enucleated kidneys were divided into two groups. One group was treated with the composition 1 solution and the other group was treated with the composition 2 solution. That is, each kidney was irrigated with 250 ml of the composition 1 or 2 solution kept at 4° C. and was then stored in the rest of the solution for 72 hours.

Thereafter, each kidney was flushed with a solution of Lactec(trade name) having the same electrolyte composition as extracellular fluid, after which the kidney was transplanted to fosea iliaca and simultaneously the other (remaining) kidney was enucleated.

(3) Result (a) Survival Ratio

In the group treated with the composition 1 solution, only one of the total 6 dogs tested survived. In the group treated with the present solution (the composition 2 solution), all of the total 4 dogs tested survived.

(b) Serum creatinine value

As shown below, the group treated with the present solution all showed low values. (In the following table, the unit of each figure is mg/dl.)

|  | \_ Days | | | | | |
|---|---|---|---|---|---|---|
|  | −3 | 1 | 4 | 7 | 11 | 14 |
| 1 | 1.2 | 4.9 | 5.9 | 5.9 | 3.3 | 1.5 |
| 2 | 1.3 | 3.8 | 4.7 | 5.1 | 2.6 | 1.3 |
| Control |  |  | 5–7 | 10–12 | 18–20 | + |

In the above table, the figures in the left (1 and 2) each indicate the control number of mongrel dog in the group tested with the present solution. The serum creatinine values are normal at 0.8–1.3 mg/dl.

Similar results were obtained also when other organogermanium compound of the formula (I) were used as the effective component of the present solution.

As appreciated from the above description, the present solution is very excellent as a solution for washing and storing separated organs.

What is claimed is:

1. A solution for washing and storing separated organs, said solution comprising a hypertonic electrolyte solution and an effective washing and storing amount of an organogermanium compound represented by the formula (I):

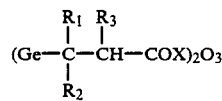

wherein $R_1$ to $R_3$ are each a hydrogen atom, a lower alkyl group which may be the same or different, or a substituted or unsubstituted phenyl group, and X is a hydroxyl group, an O-lower alkyl group, an amino group or $O^-Y^+$ wherein Y is a metal or a basic group-containing compound.

2. The solution according to claim 1, wherein the hypertonic electrolyte solution is an electrolyte solution having the same composition as intracellular fluid.

3. The solution according to claim 2, wherein the electrolyte solution having the same composition as intracellular fluid is a Collins solution.

4. The solution according to claim 2, wherein the electrolyte solution having the same composition as intracellular fluid is an Euro Collins solution.

5. The solution according to claim 2, wherein the electrolyte solution contains at least $Na^+$, $K^+$, $Cl^-$, $HCO_3^-$, $HPO_4^{--}$, $H_2PO_4^-$.

6. The solution according to claim 1, wherein $R_1$, $R_2$ and $R_3$ are a hydrogen atom and X is a hydroxyl group.

7. The solution according to claim 1, further comprising heparin, procaine, furosemide and mannitol.

8. The solution according to claim 1, wherein the lower alkyl group is a methyl or an ethyl group.

9. The solution according to claim 1, wherein the metal is sodium or potassium.

10. The solution according to claim 1, wherein the basic group is a lysozyme or a basic amino acid.

11. A method for organ preservation comprising the steps of:

(a) washing a separated organ with a solution comprising a crystalloid solution and an effective washing and storing amount of an organogermanium compound represented by the formula (I):

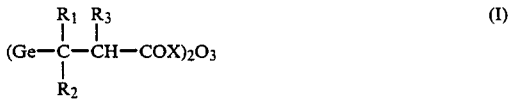

wherein $R_1$ to $R_3$ are each a hydrogen atom, a lower alkyl group which may be the same or different, or a substituted or unsubstituted phenyl group, and X is a hydroxyl group, an O-lower alkyl group, an amino group or $O^-Y^+$ wherein Y is a metal or a basic group containing compound; and (b) storing the separated organ in the solution.

12. The method according to claim 11, wherein $R_1$, $R_2$ and $R_3$ are a hydrogen atom and X is a hydroxyl group.

13. The method according to claim 11, wherein said solution further comprises heparin, procaine, furosemide and mannitol.

14. The method according to claim 11, wherein the lower alkyl group is a methyl or an ethyl group.

15. The method according to claim 11, wherein the metal is sodium or potassium.

16. The method according to claim 11, wherein the basic group is a lysozyme or a basic amino acid.

* * * * *